(12) United States Patent
Satake et al.

(10) Patent No.: US 8,722,906 B2
(45) Date of Patent: May 13, 2014

(54) (E)-N-MONOALKYL-3-OXO-3-(2-THIENYL) PROPENAMINE AND PROCESS FOR PRODUCING THE SAME AND PROCESS FOR PRODUCING (E,Z)-N-MONOALKYL-3-OXO-3-(2-THIENYL) PROPENAMINE

(75) Inventors: Syuzo Satake, Hyogo (JP); Noriyuki Hayashizaka, Hyogo (JP); Ichiro Fuseya, Hyogo (JP); Muneaki Tanaka, Hyogo (JP); Hirokazu Kagano, Hyogo (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 0 days.

(21) Appl. No.: 13/396,972

(22) Filed: Feb. 15, 2012

(65) Prior Publication Data

US 2012/0149917 A1    Jun. 14, 2012

Related U.S. Application Data

(62) Division of application No. 11/989,100, filed as application No. PCT/JP2006/315226 on Aug. 1, 2006, now Pat. No. 8,183,392.

(30) Foreign Application Priority Data

Aug. 19, 2005   (JP) .................................. 2005-238917

(51) Int. Cl.
    *C07D 333/22*   (2006.01)
(52) U.S. Cl.
    CPC ................................... *C07D 333/22* (2013.01)
    USPC .......................................................... 549/72
(58) Field of Classification Search
    CPC .................................................... C07D 333/22
    USPC .......................................................... 549/72
    See application file for complete search history.

(56) References Cited

U.S. PATENT DOCUMENTS

2004/0082794 A1    4/2004   Yokozawa et al.
2005/0240030 A1   10/2005   Kogami et al.

FOREIGN PATENT DOCUMENTS

| EP | 1 411 045 A1 | 4/2004 |
| EP | 1 541 569 A1 | 6/2005 |
| JP | 02-202865 A | 8/1990 |
| JP | 07-188065 A | 7/1995 |
| JP | A-2004-155770 | 6/2004 |
| WO | WO 2004/016603 A1 | 2/2004 |
| WO | WO 2004/103990 A1 | 12/2004 |

OTHER PUBLICATIONS

Havlin et al., PNAS, 2005, v. 102, p. 3284-89.*
Miyoshi et al., Macromolecules 2002, 35, p. 2624-2632.*
Office Action dated Sep. 1, 2010 in corresponding Chinese Patent Application No. 200680029881.3 (English translation enclosed).
Extended European Search Report dated Aug. 12, 2009 issued from the European Patent Office in the corresponding European patent application No. 06782103.3-1521.
Flood et al. "Mutarotation of D-fructose in aqueous-ethanolic solutions and its influence on crystallization" *Carbohydrate Research*, 288 (1996), 45-56.
International Search Report mailed Sep. 12, 2006 in International Application No. PCT/JP2006/315226.
Gupton, John T. et al., "The Preparation of Thiophene Appended Vinylogous Iminium Salts and Their Application to the Regioselective Synthesis of Thienylpyrimidines and Thienylpyrroles," *Heterocycles*, vol. 37, No. 1, 1994, pp. 487-499.
Bastianelli, Carlo et al., "Thermal Isomerization of Photochemically Synthesized (Z)-9-Styrylacridines. An Unusually High Enthalpy of Z→E Conversion for Stilbene-like Compounds," *Journal of the Chemical Society*, Perkin Transactions 2: Physical Organic Chemistry, No. 5, 1991, pp. 679-683.
Liu, Huiling, et al., "Chemo-Enzymatic Synthesis of the Antidepressant Duloxetine and Its Enantiomer", *Chirality*, 12:26-29 (2000).
Office Action mailed Oct. 27, 2010 issued by the US Patent Office in U.S. Appl. No. 11/989,100.
Final Office Action mailed May 24, 2011 issued by the US Patent Office in U.S. Appl. No. 11/989,100.
Notice of Allowance mailed Feb. 1, 2012 issued by the US Patent Office in U.S. Appl. No. 11/989,100.
Chemical Abstracts, vol. 79, pp. 295 (2 pages) cited in an Office Action dated Aug. 14, 2012 for the corresponding Japanese Patent Application No. 2007-530942.
Tetrahedron, vol. 40, No. 10, pp. 1835-1844 (and partial English translation) cited in an Office Action dated Aug. 14, 2012 for the corresponding Japanese Patent Application No. 2007-530942.

* cited by examiner

*Primary Examiner* — Robert Havlin
(74) *Attorney, Agent, or Firm* — Posz Law Group, PLC

(57) ABSTRACT

The present invention provides a process for producing (E)-N-monoalkyl-3-oxo-3-(2-thienyl)propenamine represented by Formula (1);

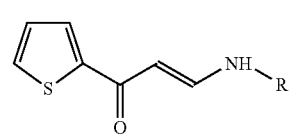

(1)

wherein R is a $C_{1-4}$ alkyl,
the method comprising the steps of:
maintaining a solution containing (Z)—N-monoalkyl-3-oxo-3-(2-thienyl)propenamine dissolved therein at 25° C. or below to deposit crystals and separating crystals having a particle diameter of 100 μm or less from the deposited crystals; and a process for producing (E,Z)—N-monoalkyl-3-oxo-3-(2-thienyl)propenamine comprising the steps of:
reacting an alkali metal salt of β-oxo-β-(2-thienyl)propanal with a monoalkylamine compound; adding a water-insoluble organic solvent to the resulting reaction mixture; adding seed crystals containing (E)-N-monoalkyl-3-oxo-3-(2-thienyl)propenamine to an organic layer obtained by conducting separation; and keeping the resulting mixture at 25° C. or below.

6 Claims, No Drawings

(E)-N-MONOALKYL-3-OXO-3-(2-THIENYL) PROPENAMINE AND PROCESS FOR PRODUCING THE SAME AND PROCESS FOR PRODUCING (E,Z)-N-MONOALKYL-3-OXO-3-(2-THIENYL) PROPENAMINE

CROSS REFERENCE TO RELATED APPLICATIONS

This application is a divisional application of U.S. patent application Ser. No. 11/989,100 filed on Jan. 22, 2008, now U.S. Pat. No. 8,183,392 B2, which in turn is a PCT National Stage application of PCT International Application No. PCT/JP2006/315226 filed on Aug. 1, 2006, which claims priority from Japanese Application No. 2005-238917 filed on Aug. 19, 2005, the contents of each being incorporated herein by reference.

TECHNICAL FIELD

The present invention relates to (E)-N-monoalkyl-3-oxo-3-(2-thienyl)propenamines and a process for producing the same, and a process for producing (E,Z)—N-monoalkyl-3-oxo-3-(2-thienyl)propenamines.

(E,Z)—N-Monoalkyl-3-oxo-3-(2-thienyl)propenamine is a compound useful as an intermediate in the production of medicines, etc.

BACKGROUND ART

Various methods are known as processes for producing N-monoalkyl-3-hydroxy-3-(2-thienyl)propanamines, which are important for use as production intermediates for medicines, etc.

For example, a method is known wherein 1-(2-thienyl)-3-chloropropan-1-one is reduced using sodium borohydride in ethanol to obtain 3-chloro-1-(2-thienyl)-1-propanol, halogen exchange is subsequently conducted in acetone using sodium iodide to obtain 3-iodo-1-(2-thienyl)-1-propanol, and then this is reacted with a monomethylamine aqueous solution in tetrahydrofuran (CHIRALITY, 12, 26-29 (2000)). However, since the raw material used in this method is 1-(2-thienyl)-3-chloropropan-1-one, which is a very unstable compound, this method is not industrially applicable.

One example of a known method for producing N,N-dimethyl-3-hydroxy-3-(2-thienyl)propanamine uses the reaction between 2-acetylthiophene and dimethylamine hydrochloride in isopropanol in the presence of paraformaldehyde and hydrochloric acid to obtain (2-thienyl)(2-dimethylaminoethyl)ketone, and the (2-thienyl)(2-dimethylaminoethyl)ketone is reduced using sodium borohydride in ethanol (JP 7-188065 A). If N-monoalkyl-3-hydroxy-3-(2-thienyl)propanamine is produced in the same method as described above except that a monoalkylamine hydrochloride is used instead of the dimethylamine hydrochloride, since the production intermediate, i.e., (2-thienyl)(2-monoalkylaminoethyl)ketone, is unstable, an N,N',N''-alkyl-bis[1-[3-oxo-3-(2-thienyl)propane]]amine, which is a dimer, is produced, and therefore the yield of the N-monoalkyl-3-hydroxy-3-(2-thienyl) propanamine obtained after the reduction using sodium borohydride is low.

A method wherein an N-monoalkyl-3-hydroxy-3-(2-thienyl)propanamine is obtained by reducing a (Z)—N-monoalkyl-3-oxo-3-(2-thienyl)propenamine is also known (WO 2004/016603 A1). Therefore, there is a strong demand for a method for efficiently producing an (E,Z)—N-monoalkyl-3-oxo-3-(2-thienyl)propenamine, which is a raw material for N-monoalkyl-3-hydroxy-3-(2-thienyl)propanamines.

DISCLOSURE OF THE INVENTION

Problem to be Solved by the Invention

An object of the present invention is to provide a method for readily producing an (E,Z)—N-monoalkyl-3-oxo-3-(2-thienyl)propenamine at a high yield, and an (E)-N-monoalkyl-3-oxo-3-(2-thienyl)propenamine used in such a method and a method for producing the same.

Means for Solving the Problem

The present invention provides the (E)-N-monoalkyl-3-oxo-3-(2-thienyl)propenamine shown below and a method for producing the same, and a method for producing an (E,Z)—N-monoalkyl-3-oxo-3-(2-thienyl)propenamine.

1. An (E)-N-monoalkyl-3-oxo-3-(2-thienyl)propenamine represented by Formula (1);

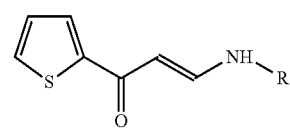

(1)

wherein R is a $C_{1-4}$ alkyl.

2. The (E)-N-monoalkyl-3-oxo-3-(2-thienyl)propenamine according to Item 1, wherein R in Formula (1) is methyl.

3. A method for producing an (E)-N-monoalkyl-3-oxo-3-(2-thienyl)propenamine represented by Formula (1);

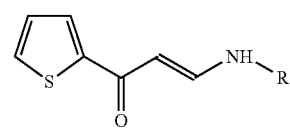

(1)

wherein R is a $C_{1-4}$ alkyl;
the method comprising the steps of:
dissolving (Z)—N-monoalkyl-3-oxo-3-(2-thienyl)propenamine, represented by Formula (2), in a solvent;

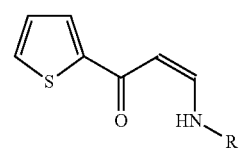

(2)

wherein R is as defined above;
subjecting the resulting solution to crystallization by keeping it at 25° C. or below; and
separating crystals having a particle diameter of 100 μm or less from the deposited crystals.

4. The method according to Item 3, wherein the solvent is methyl tert-butyl ether.

5. A method for producing an (E,Z)—N-monoalkyl-3-oxo-3-(2-thienyl)propenamine comprising the steps of:

reacting an alkali metal salt of β-oxo-β-(2-thienyl)propanal represented by Formula (3);

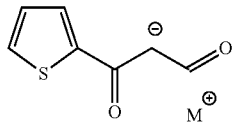

wherein M is an alkali metal atom, with a monoalkylamine compound represented by Formula (4);

wherein R is a $C_{1-4}$ alkyl;

adding a water-insoluble organic solvent to the resulting reaction mixture;

adding seed crystals containing (E)-N-monoalkyl-3-oxo-3-(2-thienyl)propenamine represented by Formula (1);

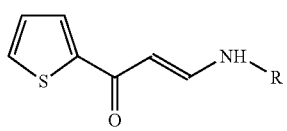

wherein R is as defined above, to an organic layer obtained by conducting separation; and keeping the resulting mixture at 25° C. or below.

6. The method according to Item 5, wherein the water-insoluble organic solvent is methyl tert-butyl ether.

The present invention is explained in detail below.

The (E)-N-monoalkyl-3-oxo-3-(2-thienyl)propenamine of the present invention is a novel compound represented by Formula (1);

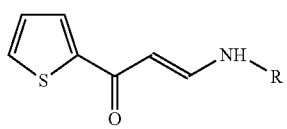

wherein R is a $C_{1-4}$ alkyl. Examples of $C_{1-4}$ alkyls include methyl, ethyl, n-propyl, isopropyl, n-butyl, and tert-butyl, etc. Among these, methyl is preferable.

Specific examples of the (E)-N-monoalkyl-3-oxo-3-(2-thienyl)propenamines include (E)-N-monomethyl-3-oxo-3-(2-thienyl)propenamine, (E)-N-monoethyl-3-oxo-3-(2-thienyl)propenamine, (E)-N-mono(n-propyl)-3-oxo-3-(2-thienyl)propenamine, (E)-N-monoisopropyl-3-oxo-3-(2-thienyl)propenamine, (E)-N-mono(n-butyl)-3-oxo-3-(2-thienyl)propenamine, (E)-N-mono(tert-butyl)-3-oxo-3-(2-thienyl)propenamine, etc.

The (E)-N-monoalkyl-3-oxo-3-(2-thienyl)propenamine represented by Formula (1) can be obtained by dissolving a (Z)—N-monoalkyl-3-oxo-3-(2-thienyl)propenamine, represented by Formula (2), in a solvent;

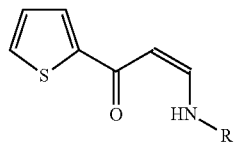

wherein R is a $C_{1-4}$ alkyl;

subjecting the resulting solution to crystallization by keeping it at 25° C. or below; and separating crystals having a particle diameter of 100 μm or less from the deposited crystals.

The (Z)—N-monoalkyl-3-oxo-3-(2-thienyl)propenamine represented by Formula (2) can be obtained by, for example, reacting an alkali metal salt of β-oxo-β-(2-thienyl)propanal represented by Formula (3);

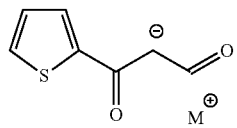

wherein M is an alkali metal atom, such as a lithium atom, sodium atom, and potassium atom, with a monoalkylamine compound represented by Formula (4);

wherein R is a $C_{1-4}$ alkyl;

in methanol or like reaction solvent.

There is no limitation to the method for producing the alkali metal salt of β-oxo-β-(2-thienyl)propanal. An example of the applicable method is that a 2-acetylthiophene and an alkali metal methoxide are reacted in an ethyl formate (JP 2-202865 A).

Specific examples of monoalkylamine compounds include monomethylamine, monoethylamine, mono(n-propyl)amine, monoisopropylamine, mono(n-butyl)amine, mono(tert-butyl)amine, etc. Hydrochlorides and sulfates of the above-mentioned monoalkylamines can also be used as the monoalkylamine compound.

The preferable amount of the monoalkylamine compound is one to fivefold moles relative to an alkali metal salt of β-oxo-β-(2-thienyl)propanal. The preferable amount of the reaction solvent is 10 to 3,000 parts by weight per 100 parts by weight of an alkali metal salt of β-oxo-β-(2-thienyl)propanal. The preferable reaction temperature is in the range of 0 to 100° C. and the preferable reaction time is in the range of 1 to 30 hours.

After the completion of the reaction, the reaction solvent is removed. Subsequently, a water-insoluble organic solvent, and, if necessary, an aqueous sodium hydroxide solution or like aqueous alkali solution that stabilizes the reaction product is added to the reaction mixture. The reaction mixture is then subjected to separation to obtain an organic layer. There is no limitation to the water-insoluble organic solvent, and usable examples thereof include toluene, ethyl acetate, methyl tert-butyl ether, etc. Among these, methyl tert-butyl ether is preferable. While maintaining the temperature of the thus-obtained organic layer at higher than 25° C., the water-insoluble organic solvent contained therein is removed. The deposited crystals are washed and dried, isolating the (Z)—N-monoalkyl-3-oxo-3-(2-thienyl)propenamine. After the completion of the reaction, for example, when the water-insoluble organic solvent is added, it is preferable that the pH of the reaction mixture be made 7 or greater in order to stabilize the reaction product by adding an aqueous alkali solution, such as an aqueous sodium hydroxide solution.

The (E)-N-monoalkyl-3-oxo-3-(2-thienyl)propenamine of the present invention can be obtained by, for example, dissolving the thus-obtained (Z)—N-monoalkyl-3-oxo-3-(2-thienyl)propenamine in a solvent, subjecting the resulting mixture to crystallization by maintaining its temperature at 25° C. or below, and isolating the crystals having a particle diameter of 100 μm or less from the deposited crystals.

There is no limitation to the solvent dissolving the (Z)—N-monoalkyl-3-oxo-3-(2-thienyl)propenamine, and usable examples thereof include pentane, hexane, cyclohexane, heptane and like aliphatic hydrocarbons; benzene, toluene, xylene, chlorobenzene and like aromatic hydrocarbons; methyl tert-butyl ether, diethylether, tetrahydrofuran, dioxane and like ethers; methanol, ethanol and like alcohols; methyl acetate, ethyl acetate, butyl acetate and like esters. Among these, methyl tert-butyl ether is preferable.

The amount of the solvent is preferably in the range of 10 to 3,000 parts by weight, and more preferably in the range of 50 to 2,000 parts by weight per 100 parts by weight of (Z)—N-monoalkyl-3-oxo-3-(2-thienyl)propenamine. If the amount of the solvent is less than 10 parts by weight, the yield may become unduly low. In contrast, if the amount of the solvent exceeds 3,000 parts by weight, the volume efficiency may be lowered.

The crystals can be separated from a solution obtained by dissolving a (Z)—N-monoalkyl-3-oxo-3-(2-thienyl)propenamine in a solvent preferably by agitating the solution. Here, standard agitation methods, such as using an agitator, etc., can be employed. There is no limitation to the agitation time, but it is preferable that the agitation time fall within the range of 5 to 30 hours.

The method of crystallizing (E)-N-monoalkyl-3-oxo-3-(2-thienyl)propenamine is not limited, and an evacuation method, a cooling method, etc., can be employed. Even when the amount of the (Z)—N-monoalkyl-3-oxo-3-(2-thienyl) propenamine exceeds the solubility to the above-mentioned solvent, i.e., in the state of supersaturation, and a solution containing solids of (Z)—N-monoalkyl-3-oxo-3-(2-thienyl) propenamine is agitated, (E)-N-monoalkyl-3-oxo-3-(2-thienyl)propenamine is crystallized at a temperature of 25° C. or below.

The particular reason of (E)-N-monoalkyl-3-oxo-3-(2-thienyl)propenamine crystallizing under the specific conditions in the present invention is not defined; however, it is believed that because the solubility of (E)-N-monoalkyl-3-oxo-3-(2-thienyl)propenamine to specific solvents is smaller than that of (Z)—N-monoalkyl-3-oxo-3-(2-thienyl)propenamine.

The deposits obtained by subjecting a (Z)—N-monoalkyl-3-oxo-3-(2-thienyl)propenamine solution to crystallization are usually (E,Z)—N-monoalkyl-3-oxo-3-(2-thienyl)propenamine containing (E)-N-monoalkyl-3-oxo-3-(2-thienyl) propenamine and (Z)—N-monoalkyl-3-oxo-3-(2-thienyl) propenamine. Crystals of (E)-N-monoalkyl-3-oxo-3-(2-thienyl)propenamine are generally smaller than those of (Z)—N-monoalkyl-3-oxo-3-(2-thienyl)propenamine, and therefore the (E)-N-monoalkyl-3-oxo-3-(2-thienyl)propenamine contained in the (E,Z)—N-monoalkyl-3-oxo-3-(2-thienyl)propenamine can be separated by using a sieve having openings of 100 μm.

The present invention also provides a method by which (E,Z)—N-monoalkyl-3-oxo-3-(2-thienyl)propenamine is readily and efficiently produced. The method includes the steps of adding a water-insoluble organic solvent to a reaction mixture obtained by reacting an alkali metal salt of β-oxo-β-(2-thienyl)propanal with a monoalkylamine compound; separating an organic layer from the reaction mixture; adding seed crystals that contain (E)-N-monoalkyl-3-oxo-3-(2-thienyl)propenamine to the organic layer; and keeping the mixture at a temperature of 25° C. or below. There is no limitation to the water-insoluble organic solvent, and toluene, ethyl acetate, methyl tert-butyl ether, etc., can be used. Among these, methyl tert-butyl ether is preferable.

It is also possible to obtain (E,Z)—N-monoalkyl-3-oxo-3-(2-thienyl)propenamine readily and effectively by adding seed crystals that contain (E)-N-monoalkyl-3-oxo-3-(2-thienyl)propenamine to a solution prepared by dissolving pre-prepared (Z)—N-monoalkyl-3-oxo-3-(2-thienyl)propenamine in a solvent, and then keeping the temperature thereof at 25° C. or below. There is no limitation to the solvent in which the (Z)—N-monoalkyl-3-oxo-3-(2-thienyl)propenamine is dissolved, and water-insoluble organic solvents, such as toluene, ethyl acetate, and methyl tert-butyl ether, can be used. Among these, methyl tert-butyl ether is preferable. The amount of the solvent is preferably in the range of 10 to 3,000 parts by weight, and more preferably in the range of 50 to 2,000 parts by weight per 100 parts by weight of (Z)—N-monoalkyl-3-oxo-3-(2-thienyl)propenamine.

There is no limitation to the method for depositing (E,Z)—N-monoalkyl-3-oxo-3-(2-thienyl)propenamine by addition of seed crystals, and an evacuation method, a cooling method, etc., can be employed.

The amount of the seed crystals is preferably 0.01 to 0.5 mol. %, and more preferably 0.01 to 0.1 mol. % per (Z)—N-monoalkyl-3-oxo-3-(2-thienyl)propenamine dissolved in the solvent. If the amount of the (E)-N-monoalkyl-3-oxo-3-(2-thienyl)propenamine used as seed crystals is less than 0.01 mol. %, the (E)-N-monoalkyl-3-oxo-3-(2-thienyl)propenamine may not function as seed crystals and the yield may be lowered. In contrast, if the amount of the (E)-N-monoalkyl-3-oxo-3-(2-thienyl)propenamine exceeds 0.5 mol. %, the effect that is commensurate with the amount of the (E)-N-monoalkyl-3-oxo-3-(2-thienyl)propenamine cannot be obtained and it may be uneconomical.

By reducing the thus-obtained (E,Z)—N-monoalkyl-3-oxo-3-(2-thienyl)propenamine, N-monoalkyl-3-hydroxy-3-(2-thienyl)propanamine can be produced.

Examples of the reducing agents usable in the reduction include sodium borohydride, sodium borohydride-cyanide, etc. An example of a usable reaction solvent is toluene. The reaction temperature is preferably in the range of 20 to 100° C. The reaction time is preferably in the range of 1 to 30 hours. Proton sources, such as acetic acid, may be used if necessary. When a water-insoluble solvent is used as a reaction solvent, N-monoalkyl-3-hydroxy-3-(2-thienyl)propanamine can be isolated by adding water to conduct separation after the completion of the reaction, removing the solvent in the organic layer that was obtained by the separation, and recrystallizing the deposited crystals.

Effects of the Invention

The present invention makes it possible to easily obtain (E,Z)—N-monoalkyl-3-oxo-3-(2-thienyl)propenamine, which is useful as an intermediate in the production of medicines, at a high yield.

BEST MODE FOR CARRYING OUT THE INVENTION

The present invention is explained in detail below with reference to Examples and Comparative Examples. However, the present invention is not limited to these Examples.

Production Example 1

In a 1-liter four-necked flask equipped with an agitator, a condenser, a thermometer, and a dropping funnel were placed 88.1 g (0.50 mol.) of sodium salt of β-oxo-β-(2-thienyl)propanal and 168 g of methanol. A 38.5 wt. % aqueous monomethylamine hydrochloride solution (87.8 g, 0.50 mol.) was then added thereto dropwise at 25° C. over 20 minutes. After the completion of the addition, the resulting mixture was allowed to react at 30° C. for 5 hours.

After the completion of the reaction, methanol was removed. Thereafter, 121.4 g of 3.1 wt. % aqueous sodium hydroxide solution and 300 g of methyl tert-butyl ether were added thereto, and then the resulting mixture was subjected to separation. While maintaining the temperature of the thus-obtained organic layer at 40° C., the solvent was removed and the deposited crystals were separated by filtration. The thus-obtained crystals were washed with 100 g of ethanol twice and then dried, obtaining 62.5 g (0.374 mol.) of (Z)—N-monomethyl-3-oxo-3-(2-thienyl)propenamine. The yield of the (Z)—N-monomethyl-3-oxo-3-(2-thienyl)propenamine was 74.8% relative to the sodium salt of β-oxo-β-(2-thienyl)propanal.

It was confirmed that the thus-obtained crystals were (Z)—N-monomethyl-3-oxo-3-(2-thienyl)propenamine by the following analysis results.

Molecular weight: 167.23
Melting point: 85.3-86.4° C.
Elemental analysis: C, 57.23%; H, 5.55%; N, 8.38% (theoretical values: C, 57.46%; H, 5.42%; N, 8.37%)
Infrared absorption spectrum (KBr, cm$^{-1}$): 3230, 3079, 3064, 2929, 2904, 2813, 1629, 1552, 1513, 1488, 1427, 1413, 1351, 1290, 1251, 1234, 1176, 1145, 1093, 1060, 1012, 979, 954, 856, 842, 759, 740, 698, 663, 565, 468, 453
$^1$H-nuclear magnetic resonance spectrum (CDCl$_3$, TMS base) δ (ppm): 9.90 (b, 1H), 7.54 (dd, 1H), 7.45 (dd, 1H), 7.06 (dd, 1H), 6.85 (dd, 1H), 5.57 (d, 1H), 3.05 (d, 3H)
Solid NMR$^{13}$C-nuclear magnetic resonance spectrum (TMS base) δ (ppm): 39.11, 91.08, 129.70, 132.25, 134.21, 149.51, 158.53, 184.80.

Example 1

To a 1-liter four-necked flask equipped with an agitator, a condenser, a thermometer, and a dropping funnel were placed 83.6 g (0.50 mol.) of (Z)—N-monomethyl-3-oxo-3-(2-thienyl)propenamine obtained in the same manner as in Production Example 1 and 332.2 g of methyl tert-butyl ether. The mixture was agitated at 25° C. for 5 hours and then subjected to crystallization.

The deposited crystals were subjected to filtration, washed with 100 g of methyl tert-butyl ether twice and then dried, obtaining 70.2 g (0.42 mol.) of (E,Z)—N-monomethyl-3-oxo-3-(2-thienyl)propenamine. By conducting separation using a sieve having openings of 100 μm, 3.5 g (0.02 mol.) of (E)-N-monomethyl-3-oxo-3-(2-thienyl)propenamine was obtained. The yield of the thus-obtained (E)-N-monomethyl-3-oxo-3-(2-thienyl)propenamine was 4.2% relative to the (Z)—N-monomethyl-3-oxo-3-(2-thienyl)propenamine used.

It was confirmed that the thus-separated crystals (crystals having a particle diameter of 100 μm or less) were (E)-N-monomethyl-3-oxo-3-(2-thienyl)propenamine based on the following analysis results.

Molecular weight: 167.23
Melting point: 65-66° C.
Elemental analysis: C, 57.23%; H, 5.55%; N, 8.38% (theoretical values: C, 57.46%; H, 5.42%; N, 8.37%)
Infrared absorption spectrum (KBr, cm$^{-1}$): 3230, 3079, 3064, 2929, 2813, 1824, 1766, 1629, 1552, 1513, 1488, 1413, 1351, 1290, 1251, 1234, 1176, 1145, 1093, 1060, 1012, 979, 954, 842, 804, 759, 740, 698, 663, 565, 468, 453
Solid NMR$^{13}$C-nuclear magnetic resonance spectrum (TMS base) δ (ppm): 30.09, 91.08, 129.70, 132.25, 134.21, 149.51, 158.73, 184.80

Example 2

In a 1-liter four-necked flask equipped with an agitator, a condenser, a thermometer, and a dropping funnel were placed 88.1 g (0.50 mol.) of sodium salt of β-oxo-β-(2-thienyl)propanal and 168 g of methanol, and 87.8 g (0.50 mol.) of 38.5 wt. % aqueous monomethylamine hydrochloride solution was added thereto dropwise at 25° C. over 20 minutes. After the completion of the addition, the mixture was allowed to react at 30° C. over 5 hours.

After the completion of the reaction, the methanol was removed. After adding 121.4 g of 3.1 wt. % aqueous sodium hydroxide solution and 300 g of methyl tert-butyl ether, the mixture was subjected to separation. The thus-separated organic layer was cooled, and 0.01 g of (E)-N-monomethyl-3-oxo-3-(2-thienyl)propenamine obtained in Example 1 was added thereto at 25° C. as seed crystals. After cooling the organic layer to −5° C., the deposited crystals were subjected to filtration. The thus-obtained crystals were washed with 100 g of ethanol twice and then dried, obtaining 70.2 g (0.42 mol.) of (E,Z)—N-monomethyl-3-oxo-3-(2-thienyl)propenamine. The yield of the thus-obtained (E,Z)—N-monomethyl-3-oxo-3-(2-thienyl)propenamine was 84% relative to the sodium salt of β-oxo-β-(2-thienyl)propanal.

The physical properties of the obtained (E,Z)—N-monomethyl-3-oxo-3-(2-thienyl)propenamine are shown below.

Molecular weight: 167.23
Melting point: 76.4-81.1° C.
Elemental analysis: C, 57.23%; H, 5.55%; N, 8.38% (theoretical values: C, 57.46%; H, 5.42%; N, 8.37%)
Infrared absorption spectrum (KBr, cm$^{-1}$): 3230, 3079, 3066, 2931, 2815, 1629, 1552, 1513, 1488, 1427, 1413, 1351, 1292, 1253, 1234, 1176, 1147, 1093, 1060, 1012, 979, 956, 842, 804, 759, 740, 700, 663, 566, 468, 453

Comparative Example 1

In a 1-liter four-necked flask equipped with an agitator, a condenser, a thermometer, and a dropping funnel were placed 88.1 g (0.50 mol.) of sodium salt of β-oxo-β-(2-thienyl)propanal and 168 g of methanol, and then 87.8 g (0.50 mol.) of 38.5 wt. % aqueous monomethylamine hydrochloride solution was added thereto dropwise at 25° C. over 20 minutes. After the completion of the addition, the mixture was then reacted at 30° C. over 5 hours.

After the completion of the reaction, methanol was removed. Thereafter, 121.4 g of 3.1 wt. % aqueous sodium hydroxide solution and 100 g of methyl tert-butyl ether were added thereto and then the mixture was subjected to separation. The organic layer obtained by separation was cooled, and 0.01 g of (Z)—N-monomethyl-3-oxo-3-(2-thienyl)propenamine obtained in Production Example 1 was added at 25° C. as seed crystals. After cooling the organic layer to −5° C., the deposited crystals were subjected to filtration. The obtained crystals were washed with 100 g of ethanol twice and then dried, obtaining 62.5 g (0.374 mol.) of (Z)—N-monomethyl-3-oxo-3-(2-thienyl)propenamine. The yield of the obtained (Z)—N-monomethyl-3-oxo-3-(2-thienyl)propenamine was 74.8% relative to the sodium salt of β-oxo-β-(2-thienyl)propanal.

It was confirmed that the obtained crystals were (Z)—N-monomethyl-3-oxo-3-(2-thienyl)propenamine by the following analysis results.

Melting point: 85.3-86.4° C.

Elemental analysis: C, 57.23%; H, 5.55%; N, 8.38% (theoretical values: C, 57.46%; H, 5.42%; N, 8.37%)

Infrared absorption spectrum (KBr, cm$^{-1}$): 3230, 3079, 3064, 2929, 2904, 2813, 1629, 1552, 1513, 1488, 1427, 1413, 1351, 1290, 1251, 1234, 1176, 1145, 1093, 1060, 1012, 979, 954, 856, 842, 759, 740, 698, 663, 565, 468, 453

$^1$H-nuclear magnetic resonance spectrum (CDCl$_3$, TMS base) δ (ppm): 9.90 (b, 1H), 7.54 (dd, 1H), 7.45 (dd, 1H), 7.06 (dd, 1H), 6.85 (dd, 1H), 5.57 (d, 1H), 3.05 (d, 3H)

Solid NMR $^{13}$C-nuclear magnetic resonance spectrum (TMS base) δ (ppm): 39.11, 91.08, 129.70, 132.25, 134.21, 149.51, 158.53, 184.80.

The invention claimed is:

1. An (E)-N-monoalkyl-3-oxo-3-(2-thienyl) propenamine represented by Formula (1);

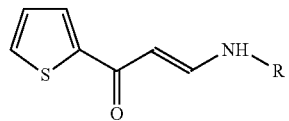

(1)

wherein R is a C$_{1-4}$ alkyl.

2. The (E)-N-monoalkyl-3-oxo-3-(2-thienyl) propenamine according to claim 1, wherein R in Formula (1) is methyl.

3. A method for producing an (E,Z)-N-monoalkyl-3-oxo-3-(2-thienyl) propenamine comprising the steps of:

reacting an alkali metal salt of β-oxo-β-(2-thienyl) propanal represented by Formula (3);

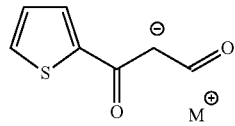

(3)

wherein M is an alkali metal atom, with a monoalkylamine compound represented by Formula (4);

H$_2$N—R  (4), wherein R is a C$_{1-4}$ alkyl;

adding a water-insoluble organic solvent to the resulting reaction mixture;

adding seed crystals containing (E)-N-monoalkyl-3-oxo-3-(2-thienyl) propenamine represented by Formula (1);

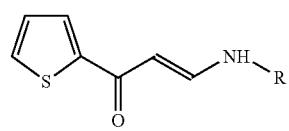

(1)

wherein R is as defined above, to an organic layer obtained by conducting separation; and keeping the resulting mixture at 25° C. or below.

4. The method according to claim 3, wherein the water-insoluble organic solvent is methyl tert-butyl ether.

5. The (E)-N-monoalkyl-3-oxo-3-(2-thienyl) propenamine represented by Formula (1) according to claim 1, which is prepared by a method comprising steps of:

dissolving (Z)-N-monoalkyl-3-oxo-3-(2-thienyl) propenamine, represented by Formula (2), in a solvent;

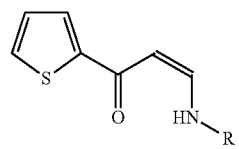

(2)

wherein R is as defined above;

subjecting the resulting solution to crystallization by keeping it at 25° C. or below; and separating crystals having a particle diameter of 100 μm or less from the deposited crystals.

6. The (E)-N-monoalkyl-3-oxo-3-(2-thienyl) propenamine represented by Formula (1) and prepared by the method of claim 5, wherein the solvent is methyl tert-butyl ether.

* * * * *